(12) United States Patent
Cheung

(10) Patent No.: US 7,256,026 B2
(45) Date of Patent: Aug. 14, 2007

(54) ORAL COMPOSITIONS FOR WHITE BLOOD CELL ACTIVATION AND PROLIFERATION

(75) Inventor: Ling Yuk Cheung, Hong Kong (HK)

(73) Assignee: Ultra Biotech Limited, Douglas (IM)

( * ) Notice: Subject to any disclaimer, the term of this patent is extended or adjusted under 35 U.S.C. 154(b) by 508 days.

(21) Appl. No.: 10/185,276

(22) Filed: Jun. 28, 2002

(65) Prior Publication Data

US 2004/0005680 A1    Jan. 8, 2004

(51) Int. Cl.
C12N 13/00 (2006.01)
A01N 63/04 (2006.01)
A61K 9/00 (2006.01)
A61K 47/00 (2006.01)

(52) U.S. Cl. .............................. 435/173.1; 424/195.16; 424/400; 424/439

(58) Field of Classification Search ............. 435/173.8; 424/93.51, 195.16, 400, 439
See application file for complete search history.

(56) References Cited

U.S. PATENT DOCUMENTS

| | | | |
|---|---|---|---|
| 2,107,830 A | 2/1938 | Liebesny et al. | |
| 4,348,483 A | 9/1982 | Skogerson | |
| 4,447,445 A * | 5/1984 | Jacobs et al. | 514/460 |
| 5,504,079 A | 4/1996 | Jamas et al. | |
| 5,665,352 A | 9/1997 | Blehaut et al. | |
| 6,143,731 A | 11/2000 | Jamas et al. | |
| 6,197,295 B1 | 3/2001 | Hsia et al. | |
| 6,391,617 B1 | 5/2002 | Cheung | |
| 6,391,618 B1 | 5/2002 | Cheung | |
| 6,391,619 B1 | 5/2002 | Cheung | |
| 6,416,982 B1 | 7/2002 | Zhang | |
| 6,416,983 B1 | 7/2002 | Cheung | |
| 6,436,695 B1 | 8/2002 | Cheung | |
| 6,440,713 B1 | 8/2002 | Cheung | |
| 6,596,272 B2 | 7/2003 | Cheung | |
| 6,596,273 B2 | 7/2003 | Cheung | |
| 6,649,383 B1 | 11/2003 | Cheung | |
| 6,660,508 B1 | 12/2003 | Cheung | |
| 6,709,849 B2 | 3/2004 | Cheung | |
| 6,753,008 B2 | 6/2004 | Cheung | |
| 6,756,050 B2 | 6/2004 | Cheung | |
| 6,759,055 B2 | 7/2004 | Cheung | |
| 6,761,886 B2 | 7/2004 | Cheung | |
| 6,793,933 B2 | 9/2004 | Cheung | |
| 6,800,466 B2 | 10/2004 | Cheung | |
| 6,828,131 B2 | 12/2004 | Zhang | |
| 6,828,132 B2 | 12/2004 | Cheung | |
| 2002/0099026 A1 | 7/2002 | Goodman et al. | |
| 2002/0123127 A1 | 9/2002 | Cheung | |
| 2002/0123129 A1 | 9/2002 | Cheung | |
| 2002/0123130 A1 | 9/2002 | Cheung | |
| 2003/0230126 A1 | 12/2003 | Cheung | |
| 2003/0230245 A1 | 12/2003 | Cheung | |
| 2003/0232038 A1 | 12/2003 | Cheung | |
| 2003/0232039 A1 | 12/2003 | Cheung | |
| 2003/0232059 A1 | 12/2003 | Cheung | |
| 2003/0235565 A1 | 12/2003 | Cheung | |
| 2003/0235566 A1 | 12/2003 | Cheung | |
| 2003/0235567 A1 | 12/2003 | Cheung | |
| 2003/0235568 A1 | 12/2003 | Cheung | |
| 2003/0235569 A1 | 12/2003 | Cheung | |
| 2003/0235570 A1 | 12/2003 | Cheung | |
| 2004/0001812 A1 | 1/2004 | Cheung | |
| 2004/0001813 A1 | 1/2004 | Cheung | |
| 2004/0001814 A1 | 1/2004 | Cheung | |
| 2004/0001857 A1 | 1/2004 | Cheung | |
| 2004/0001859 A1 | 1/2004 | Cheung | |
| 2004/0005335 A1 | 1/2004 | Cheung | |
| 2004/0005336 A1 | 1/2004 | Cheung | |
| 2004/0005680 A1 | 1/2004 | Cheung | |
| 2004/0168492 A1 | 9/2004 | Cheung | |
| 2004/0253251 A1 | 12/2004 | Cheung | |
| 2004/0253252 A1 | 12/2004 | Cheung | |
| 2004/0253253 A1 | 12/2004 | Cheung | |
| 2004/0253254 A1 | 12/2004 | Cheung | |
| 2004/0253255 A1 | 12/2004 | Cheung | |
| 2004/0253256 A1 | 12/2004 | Cheung | |
| 2004/0253257 A1 | 12/2004 | Cheung | |
| 2004/0253258 A1 | 12/2004 | Cheung | |
| 2004/0253259 A1 | 12/2004 | Cheung | |

(Continued)

FOREIGN PATENT DOCUMENTS

| | | |
|---|---|---|
| CN | 1309175 A | 8/2001 |
| ES | 475500 | 11/1978 |
| GB | 1 397 873 | 6/1975 |
| WO | WO 02/070682 A2 | 9/2002 |

(Continued)

OTHER PUBLICATIONS

Cabri (www.cabri.org/CABRI/srs-doc/index.html), 1997.*
U.S. Appl. No. 10/999,860, Cheung, Nov. 29, 2004.
U.S. Appl. No. 10/999,861, Cheung, Nov. 29, 2004.
Dutta SK et al. Lack of microbial genetic response to 2.45 GHz CW and 8.5- to 9.6-GHz pulsed microwaves. J Microw Power. Sep. 1979;14(3):275-80.

(Continued)

Primary Examiner—Christopher R Tate
Assistant Examiner—Randall Winston
(74) Attorney, Agent, or Firm—Jones Day

(57) ABSTRACT

The present invention relates to health food, health drink, and health supplement. The invention relates to biological compositions comprising yeast cells that can improve the immune functions of animals. The invention also relates to methods for manufacturing the biological compositions, and methods of using the biological compositions to produce a healthful benefit in a subject with immunodeficiency disorders or immunosuppression by promoting activation and proliferation of white blood cells.

4 Claims, 2 Drawing Sheets

U.S. PATENT DOCUMENTS

Figure 1:
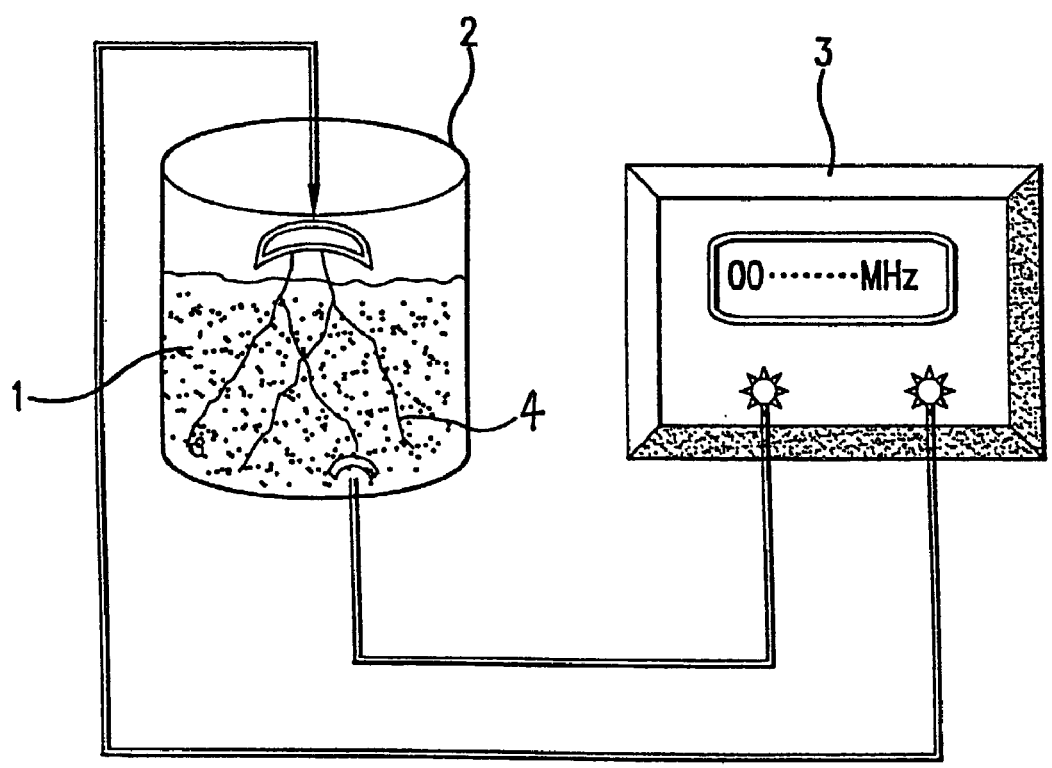

| | | |
|---|---|---|
| 2004/0253260 A1 | 12/2004 | Cheung |
| 2004/0253261 A1 | 12/2004 | Cheung |
| 2004/0253262 A1 | 12/2004 | Cheung |
| 2004/0253263 A1 | 12/2004 | Cheung |
| 2004/0253264 A1 | 12/2004 | Cheung |
| 2004/0253265 A1 | 12/2004 | Cheung |
| 2004/0253266 A1 | 12/2004 | Cheung |
| 2004/0253267 A1 | 12/2004 | Cheung |
| 2004/0265990 A1 | 12/2004 | Cheung |
| 2005/0106166 A1 | 5/2005 | Cheung |
| 2005/0106167 A1 | 5/2005 | Cheung |
| 2005/0106168 A1 | 5/2005 | Cheung |
| 2005/0106169 A1 | 5/2005 | Cheung |
| 2005/0106170 A1 | 5/2005 | Cheung |
| 2005/0106171 A1 | 5/2005 | Cheung |
| 2005/0106172 A1 | 5/2005 | Cheung |
| 2005/0106173 A1 | 5/2005 | Cheung |
| 2005/0106174 A1 | 5/2005 | Cheung |
| 2005/0106704 A1 | 5/2005 | Cheung |
| 2005/0106705 A1 | 5/2005 | Cheung |

OTHER PUBLICATIONS

"*Saccharomyces cerevisiae* Meyen ex Hansen Chinese Strain name" (http://www.im.ac.cn/database/CCCCM/YEAST/yl122.htm), Apr. 24, 1996.

WHO World Health Organization http:www.who.int/peh-emf/about/WhatisEMF/en/ and http:www.who.int/peh-emf/about/WhatisEMF/en/index3.html retrieved Jun. 10, 2004.

U.S. Appl. No. 10/184,749, filed Jun. 28, 2002, Cheung, L.Y.

Bassett CA. 1993. Beneficial effects of electromagnetic fields. J Cell Biochem. 51(4):387-393.

Born et al. 1993. *Saccharomyces boulardii* therapy of HIV associated features (2). Deutsche Medizinische Wochenschrift (Germany) 118(2):765.

Filho et al. 1998. Dose effect of oral *Saccharomyces boulardii* treatments on morbidity and mortality in immunosuppressed mice. J Med Microbio. (United Kingdom) 47(2):111-116.

Gonzalez et al. 1980. Effects of an electric field of sinusoidal waves on the amino acid biosynthesis by *Azotobacter*. Z. Naturforsch. 35c:258-261.

Goodman et al. 1995. Effects of electromagnetic fields on molecules and cells. *International Review of Cytology*. Eds. Kwang et al. Academic Press vol. 158, pp. 279-339.

Goodman et al. 1998. Magnetic field stress induces expression of *hsp70*. Cell Stress & Chaperones. 3(2):79-88.

Grospietsch et al. 1995. Stimulating effects of modulated 150 MHz electromagnetic fields on the growth of *Escherichia coli* in a cavity resonator. Bioelectrochemistry and Bioenergetics. 37:17-23.

Grundler W. 1978. Nonthermal effects of millimeter microwaves on yeast growth. Z. Naturforsch. 33c:15-22.

Grundler et al. 1982. Resonant-like dependence of yeast growth rate on microwave frequencies. Br J Cancer Suppl. 45(5):206-208.

Grundler W. 1989. Resonant microwave effect on locally fixed yeast microcolonies. Z. Naturforsch. 44c:863-866.

Grundler et al. Mechanisms of electromagnetic interaction with cellular systems. Naturwissenschafter 79:551-559.

Kim et al. 2001. Anti-stress and anti-fatigue effects of fermented rice bran. Biosci Biotechnol Biochem. 65(10):2294-2296.

Lin H. et al. 1994. Specific region of the c-myc promoter is responsive to electric and magnetic fields. J Cell Biochem. 54(3):281-288.

Moore RL. 1979. Biological effects of magnetic fields : studies with microorganisms. Can. J. Microbiol. 25:1145-1151.

Ortuno et al. 2002. 2002. Oral administration of yeast, *Saccharomyces cerevisiae*, enhances the cellular innate immune response of gilthead seabream (*Sparus aurata* L.). Vet Immunopathol. (Netherlands) 85(1-2):41-50.

Phillips JL. 1993. Effects of electromagnetic field exposure on gene transcription. J Cell Biochem. 51(4):381-386.

Romano-Spica et al. 2000. Ets1 oncogene induction by ELF-modulated 50 MHz radiofrequency electromagnetic field. Bioelectromagnetics. 21(1):8-18.

Zhang et al. 1992. Electrostimulation of the dehydrogenase system of yeast by alternating currents. Bioelectrochemistry and Bioenergetics 28:341-353.

Machado et al. 1986. Immunopharmacological effects of Saccharomyces Baulardii in Healthy Human Volunteers, Int'l J. Immunopharmac (united Kingdom) 8(3): 245-259.

Lin H et al. 1999. A Magnetic field Responsive domain in the human heptopaomter., J cell Biochem. 75: 170-176.

* cited by examiner

ORAL COMPOSITIONS FOR WHITE BLOOD CELL ACTIVATION AND PROLIFERATION

1. FIELD OF THE INVENTION

The invention relates to oral compositions comprising yeast cells that can produce a healthful benefit in a subject with immunodeficiency disorders or immunosuppression by promoting activation and proliferation of white blood cells. The invention also relates to methods for manufacturing the oral compositions, and methods of use thereof.

2. BACKGROUND OF THE INVENTION

2.1 Immunodeficiency Disorders

The immune system protects the body from potentially harmful substances such as microorganisms, toxins, cancer cells, and blood or tissues from another person. The immune system is a complex of highly specialized cells, a circulatory system (separate from blood vessels), and organs. Together, the lymphatic vessels, lymph nodes, and lymphoid tissues located in the tonsils, thymus, liver, spleen, appendix, Peyer's patches, and bone marrow, form an intricate network that repairs damages and clears infection from the body.

The major cells of the immune system are lymphocytes, which include macrophages, neutrophils, and white blood cells. Lymphocytes, as the main cells of the lymphatic system, are relatively small compared to macrophages and neutrophils. There are two major categories of white blood cells: (1) B cells, which are derived from a parent (stem) cell in the bone marrow and mature into plasma cells; and (2) T cells, which are formed when stem cells migrate from the bone marrow to the thymus, where they undergo division, maturation, and differentiation of self from nonself. Also included are natural killer cells, which are slightly larger than B and T cells and are ready to kill invading cells without requiring the maturation and education process that B and T cells need.

B cells are part of what is known as antibody-mediated or humoral immunity. When stimulated by an antigen (a foreign substance in the body that induces an immune response), B lymphocytes mature into cells that make one of the five classes of antibodies (whose receptors are specialized to bind to a specific antigen): IgM, IgG, IgA, IgE, and IgD. On the other hand, T cells, which are further subdivided into helper (CD4 positive), suppressor, and cytotoxic (CD8 positive) T cells, are responsible for cell-mediated or cellular immunity, and for stimulating B cells. Relying on unique cell surface molecules called the major histocompatibility complex (MHC) to recognize antigen fragments, T lymphocytes attack and destroy diseased cells they recognize as foreign.

Immunodeficiency disorders are a group of diverse conditions in which the immune system does not function adequately, making infections more common, recur more frequently, and causing unusually severe, and longer lasting symptoms. Immunodeficiency disorders may be present from birth (congenital) and/or may develop later in life (acquired). Some causes of acquired immunodeficiency include hereditary and metabolic diseases (e.g., diabetes, Down syndrome, kidney failure, malnutrition, sickle cell anemia), chemicals and treatments that suppress the immune system (e.g., cancer chemotherapy, coricosteroids, immunosuppressive drugs, radiation therapy), infections (e.g., chickenpox, cytomegalovirus infection, German measles, infectious mononucleosis, measles, severe bacterial or fungal infection, severe tuberculosis), blood diseases and blood-related cancer (e.g., agranulocytosis, aplastic anemia, histiocytosis, myelofibrosis, myeloma), burns, removal of the spleen, alcoholic cirrhosis, chronic hepatitis, normal aging, sarcoidosis, systemic lupus erythematosus, etc.

Some immunodeficiency disorders can be prevented or treated. Attention to diet, good hygiene, and abstinence from smoking and illegal drugs are strongly recommended. Those who are able to produce antibodies can be vaccinated with killed rather than live vaccines. Antibodies can be given before or at the first sign of an infection. Drugs that enhance the immune system include levamisole, inosiplex, and thymic hormones. Low antibody levels can be raised with infusions or injections of immune globulin. Experimental procedures, such as transplantation of fetal thymic cells and fetal liver cells, enzyme therapy, and gene therapy, have occasionally been helpful. Blood transfusions is not generally given to those with abnormal white blood cells unless the donated blood has first been irradiated to prevent attack in the recipient's blood. And a bone marrow transplant sometimes can correct a severe immune system defect.

While drug therapy, vaccines, blood transfusion, and bone marrow transplant are useful in preventing and/or controlling infectious diseases, there is a continued need to find better treatment modalities and approaches to manage immunosuppressed or immunodeficient subjects that are more effective and less toxic, especially when clinicians are giving increased attention to the quality of life of patients. The present invention provides an alternative approach to immune disorder therapy and management of immunosuppressed conditions by using an oral composition comprising yeasts to promote activation and proliferation of white blood cells.

2.2 Yeast-Based Compositions

Yeasts and components thereof have been developed to be used as dietary supplement or pharmaceuticals. However, none of the prior methods uses whole yeast cells which have been cultured in an electromagnetic field to produce a product that promotes activation and proliferation of white blood cells. The following are some examples of prior uses of yeast cells and components thereof:

U.S. Pat. No. 6,197,295 discloses a selenium-enriched dried yeast product which can be used as dietary supplement. The yeast strain *Saccharomyces boulardii* sequela PY 31 (ATCC 74366) is cultured in the presence of selenium salts and contains 300 to about 6,000 ppm intracellular selenium. Methods for reducing flu-like symptoms growth by administration of the selenium yeast product in combination with chemotherapeutic agents is also disclosed.

U.S. Pat. No. 6,143,731 discloses a dietary additive containing whole β-glucans derived from yeast, which when administered to animals and humans, provide a source of fiber in the diet, a fecal bulking agent, a source of short chain fatty acids, reduce cholesterol and LDL, and raises HDL levels.

U.S. Pat. No. 5,504,079 discloses a method of stimulating an immune response in a subject utilizing modified yeast glucans which have enhanced immunobiologic activity. The modified glucan preparations contain increased ratios of beta (1–6) to beta (1–3) glycosidic linkages relative to naturally occurring materials. The modified glucans are prepared from the cell wall of *Saccharomyces* yeasts by extracting the cells with alkali and treating the extracted glucans with acetic acid or glucanase. See also related U.S. Pat. No. 5,082,936.

U.S. Pat. No. 4,348,483 discloses a process for preparing a chromium yeast product which has a high intracellular chromium content. The process comprises allowing the yeast cells to absorb chromium under a controlled acidic pH and, thereafter inducing the yeast cells to grow by adding nutrients. The yeast cells are dried and used as a dietary supplement.

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicant and does not constitute any admission as to the correctness of the dates or contents of these documents.

3. SUMMARY OF THE INVENTION

The present invention relates to biological or oral compositions useful for treating immunodeficiency disorders or immunosuppression by promoting activation and proliferation of white blood cells. In one embodiment, the present invention provides biological compositions comprising live yeast cells which are capable of producing a healthful benefit in subjects inflicted with immunodeficiency disorders or under immunosupression. In other embodiments, the invention provides methods of making the biological compositions, and methods of using the biological compositions.

In particular, the methods of the invention comprise culturing yeast cells in the presence of a series of electromagnetic fields such that the yeast cells becomes metabolically active. The electromagnetic fields used are each defined by one of five frequency ranges and a broad range of field strength. The starting yeast cells are commercially available and/or accessible to the public, such as but not limited to *Saccharomyces cerevisiae*. The methods for making the biological compositions of the invention further comprise conditioning the activated yeast cells in plant extracts and the gastric juice of animals, while in the presence of electromagnetic fields.

The methods of manufacturing comprise expanding the number of activated and conditioned yeast cells in large scale cultures in the presence of electromagnetic fields, performing quality control measures, and packaging. Pharmaceutical compositions of the invention comprises activated and conditioned yeast cells and one or more pharmaceutically acceptable excipients or carriers. Additional ingredients, such as vitamins and/or flavors may be added to the biological compositions to form the oral compositions of the invention. Such additional carriers and ingredients can improve the healthful benefits, pharmacological properties and organoleptic characteristics of the oral compositions. During the manufacturing process, the activated, or activated and conditioned yeast cells may be dried and stored for a period of time.

The biological or oral compositions of the invention are ingested by the subject or used as an additive to be incorporated into food to be consumed by the subject. Dietary supplement and nutritional compositions comprising activated and conditioned yeast cells are encompassed by the invention. Preferably, the subject is a human being.

In various embodiments, the biological or oral compositions of the invention are used to produce a healthful benefit in a subject with immunodeficiency disorders or under immmunosuppression by promoting activation and proliferation of white blood cells.

4. BRIEF DESCRIPTION OF FIGURES

FIG. 1 Activation and conditioning of yeast cells. 1 yeast cell culture; 2 container; 3 electromagnetic field source; 4 electrode.

Figure 2:
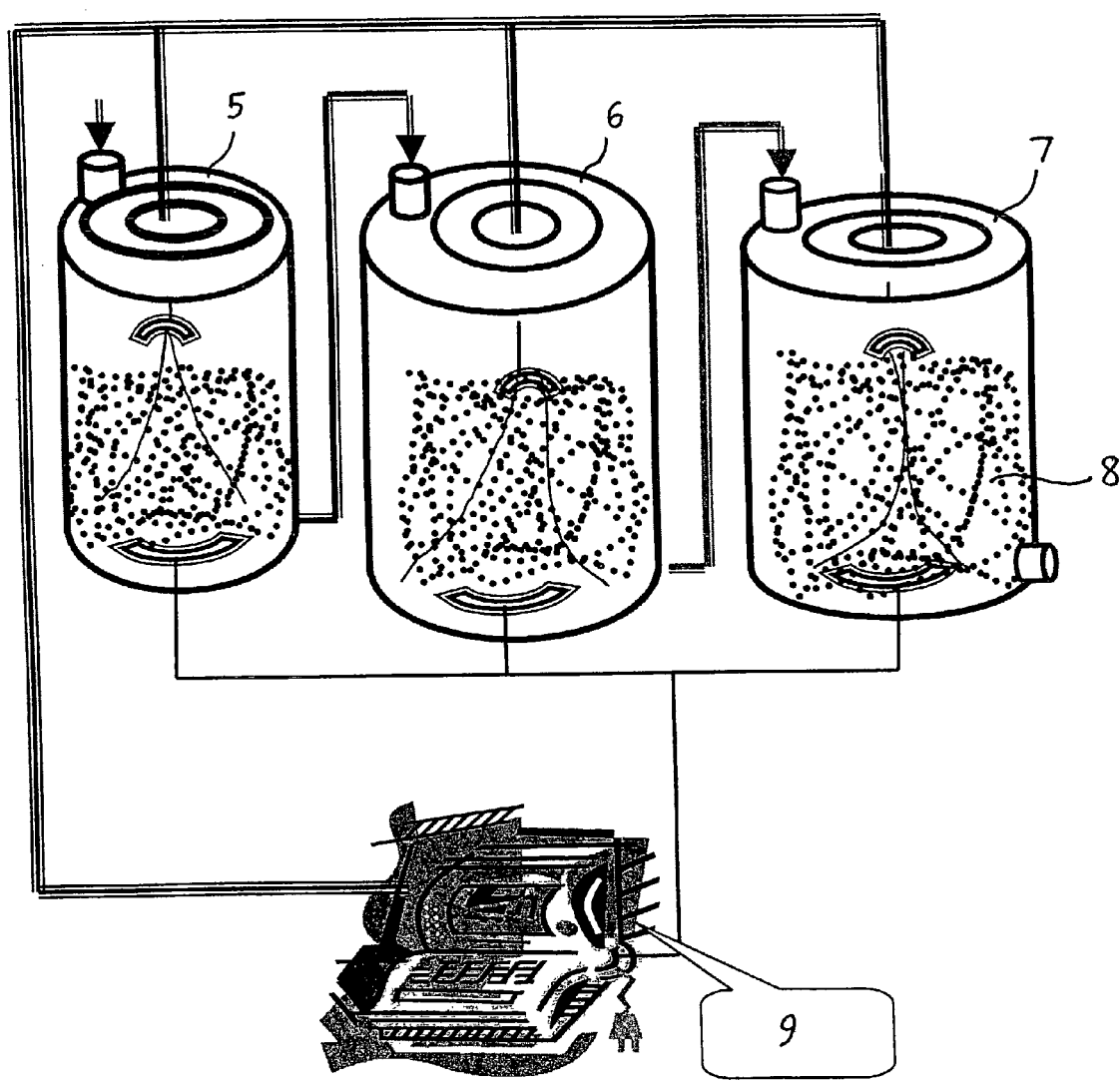

FIG. 2. Large scale propagation of yeast cells. 5 first container; 6 second container; 7 third container; 8 yeast cell cultures; 9 electromagnetic field source.

5. DETAILED DESCRIPTION OF THE INVENTION

The present invention relates to biological compositions that can produce a healthful benefit in a subject in a state of immunosuppression or immunodeficiency. The present invention provides methods for manufacturing the biological compositions as well as methods for using the biological compositions.

In one embodiment, the invention provides biological compositions that comprise yeasts. Unlike the traditional use of yeasts in the making of food, the yeast cells of the invention are not used as a source of enzymes that acts on the food ingredients The yeasts are not a primary source of nutrients for the subject. Nor are yeast cells used as a carrier, such as metal salts. The yeast cells of the invention are live when administered orally or ingested along with food by a subject. Without being bound by any theory or mechanism, the inventor believes that the culture conditions activate and/or amplified the expression of a gene or a set of genes in the yeast cells such that the yeast cells becomes highly effective in stimulating the animal's immune system, including both specific and non-specific immunological reactions. The healthful benefits provided by using the biological compositions are demonstrated in models of immunosuppression or immunodeficiency in animals which show an increase in white blood cell count.

In another embodiment, the invention provides methods for making the yeast cells in the biological compositions. The starting materials are normal yeast cells which can readily be obtained commercially or from public microorganism deposits. The methods of the invention comprise a set of culture conditions that can be applied reproducibly to activate the yeast cells. The key feature of the culture conditions used in the methods of the invention is a series of alternating electromagnetic fields of defined frequency ranges and field strengths which are applied to the growing yeast cell culture. The method further comprises the step of conditioning the activated live yeast cells to the acidic environment of the stomach of the subject. The electromagnetic fields used in these methods can be created reproducibly at various scales, thus enabling even the large scale manufacturing of the biological compositions of the invention. By careful control of the culturing conditions, normal yeast cells can be activated routinely and reproducibly to become yeast cells of the invention.

In yet another embodiment, the invention provides methods for manufacturing an oral composition comprising activated and conditioned yeasts of the invention, and additional ingredients, including but not limited to pharmaceutically acceptable carriers or excipients, vitamins, herb extracts, minerals, amino acids, flavoring agents, coloring agents, or preservatives.

In yet another embodiment, the biological compositions can be added to food which will be consumed by the subject. As known to those skilled in the relevant art, many methods may be used to mix the biological or oral compositions of the invention with food while the yeast cells remain viable.

In a particular embodiment, the culture broth comprising live yeast cells of the present invention are added directly to food just prior to consumption. Dried powders of the yeasts can also be reconstituted and added directly to food just prior to consumption.

In various embodiments, the oral compositions of the invention can be consumed directly by a subject or be fed directly to a subject. For example, the subject may drink the culture broth or a fraction thereof that comprises live activated and conditioned yeast cells. Oral compositions comprising dried yeast cells can also be given as a solid dosage form to the subject.

Although it is not necessary, the biological or oral compositions of the invention can be used in conjunction or in rotation with other types of treatment modalities, such as but not limited to surgery, chemotherapeutic agents, anti-infective drugs, blood transfusions, bone marrow transplants, vaccines, and radiation. Since the biological compositions of the invention are administered orally, the assistance of health professionals in administration of the composition is generally not essential.

Described below in Section 5.1 are the yeast cells of the invention and methods of their preparation. Section 5.2 describes the use of the biological compositions of the invention a subject suffering from immunodeficiency disorders or under immunosupression.

5.1 Preparation of the Yeast Cell Cultures

The yeast cells of the biological composition are produced by culturing a plurality of yeast cells in an appropriate culture medium in the presence of an alternating electromagnetic field over a period of time. The method comprises a first step of activating the yeast cells and a second step of conditioning the activated yeast cells. The activation process comprises culturing yeast cells in the presence of a series of five electromagnetic fields of specific frequencies and field strength. The conditioning process comprises further culturing of the activated yeast cells in a medium comprising plant extracts and extracts from the stomach of an animal, in the presence of electromagnetic fields. The activated and conditioned yeast cells can be stored as dried cells after drying the cells under appropriate conditions. The dried activated and conditioned yeast cells can be used later in large scale culturing processes for manufacturing the biological compositions of the invention. The various culturing processes of the invention can be performed either as a batch process or a continuous process.

5.1.1 Yeasts

In various embodiments, yeasts of the genera of *Saccharomyces, Candida, Crebrothecium, Geotrichum, Hansenula, Kloeckera, Lipomyces, Pichia, Rhodosporidium, Rhodotorula, Torulopsis, Trichosporon*, and *Wickerhamia* can be used in the invention. Generally, fungi used for food manufacturing are preferred.

Non-limiting examples of yeast strains include *Saccharomyces* sp., AS2.311; *Schizosaccharomyces pombe* Linder, AS2.214, AS2.248, AS2.249, AS2.255, AS2.257, AS2.259, AS2.260, AS2.274, AS2.994, AS2.1043, AS2.1149, AS2.1178, IFFI 1056; *Saccharomyces sake* Yabe, ACCC2045; *Saccharomyces uvarum* Beijer, IFFI 1023, IFFI 1032, IFFI 1044, IFFI 1072, IFFI 1205, IFFI 1207; *Saccharomyces rouxii* Boutroux, AS2.178, AS2.180, AS2.370, AS2.371; *Saccharomyces cerevisiae*Hansen Var. *ellipsoideus*, ACCC2043, AS2.2, AS2.3, AS2.8, AS2.53, AS2.163, AS2.168, AS2.483, AS2.541, AS2.559, AS2.606, AS2.607, AS2.611, AS2.612; *Saccharomyces carlsbergensis* Hansen, AS2.162, AS2.189, AS2.200, AS2.216, AS2.265, AS2.377, AS2.417, AS2.420, AS2.440, AS2.441, AS2.443, AS2.444, AS2.459, AS2.595, AS2.605, AS2.638, AS2.742, AS2.745, AS2.748, AS2.1042; *Rhodotorula aurantiaca* (Saito)Ladder; AS2.102, AS2.107, AS2.278, AS2,499, AS2,694, AS2.703, AS2.704 and AS2.1146.

*Saccharomyces cerevisiae* Hansen, ACCC2034, ACCC2035, ACCC2036, ACCC2037, ACCC2038, ACCC2039, ACCC2040, ACCC2041, ACCC2042, AS2.1, AS2.4, AS2.11, AS2.14, AS2.16, AS2.56, AS2.69, AS2.70, AS2.93, AS2.98, AS2.101, AS2.109, AS2.110, AS2.112, AS2.139, AS2.173, AS2.182, AS2.196, AS2.242, AS2.336, AS2.346, AS2.369, AS2.374, AS2.375, AS2.379, AS2.380, AS2.382, AS2.393, AS2.395, AS2.396, AS2.397, AS2.398, AS2.399, AS2.400, AS2.406, AS2.408, AS2.409, AS2.413, AS2.414, AS2.415, AS2.416, AS2.422, AS2.423, AS2.430, AS2.431, AS2.432, AS2.451, AS2.452, AS2.453, AS2.458, AS2.460, AS2.463, AS2.467, AS2.486, AS2.501, AS2.502, AS2.503, AS2.504, AS2.516, AS2.535, AS2.536, AS2.558, AS2.560, AS2.561, AS2.562, AS2.576, AS2.593, AS2.594, AS2.614, AS2.620, AS2.628, AS2.631, AS2.666, AS2.982, AS2.1190, AS2.1364, AS2.1396, IFFI 1001, IFFI 1002, IFFI 1005, IFFI 1006, IFFI 1008, IFFI 1009, IFFI 1010, IFFI 1012, IFFI 1021, IFFI 1027, IFFI 1037, IFFI 1042, IFFI 1045, IFFI 1048, IFFI 1049, IFFI 1050, IFFI 1052, IFFI 1059, IFFI 1060, IFFI 1062, IFFI 1202, IFFI 1203, IFFI 1209, IFFI 1210, IFFI 1211,IFFI 1212, IFFI 1213, IFFI 1215, IFFI 1220, IFFI 1221, IFFI 1224, IFFI 1247, IFFI 1248, IFFI 1251, IFFI 1270, IFFI 1277, IFFI 1289, IFFI 1290, IFFI 1291, IFFI 1292, IFFI 1293, IFFI 1297, IFFI 1300, IFFI 1301, IFFI 1302, IFFI 1307, IFFI 1308, IFFI 1309, IFFI 1310, IFFI 1311, IFFI 1331, IFFI 1335, IFFI 1336, IFFI 1337, IFFI 1338, IFFI 1339, IFFI 1340, IFFI 1345, IFFI 1348, IFFI 1396, IFFI 1397, IFFI 1399. Preferred yeast strains include but are not limited to *S. cerevisiae* AS2.501, AS2.502, S2.503, AS2.504, AS2.535, AS2.558, AS2.560, AS2.561, and AS2.562.

Generally, yeast strains useful for the invention can be obtained from private or public laboratory cultures, or publically accessible culture deposits, such as the American Type Culture Collection, 10801 University Boulevard, Manassas, Va. 20110-2209 and the China General Microbiological Culture Collection Center (CGMCC), China Committee for Culture Collection of Microorganisms, Institute of Microbiology, Chinese Academy of Sciences, Haidian, P.O. Box 2714, Beijing, 100080, China.

A non-limiting example of using yeast cells of the invention with *Saccharomyces cerevisiae* Hansen strain IFFI1202 is provided in Sections 6 and 7 herein below.

Although it is preferred, the preparation of the yeast cells of the invention is not limited to starting with a pure strain of yeast. The yeast cells in the biological compositions may be produced by culturing a mixture of yeast cells of different species or strains. The constituents of a mixture of yeast cells can be determined by standard yeast identification techniques well known in the art.

In various embodiments of the invention, standard techniques for handling, transferring, and storing yeasts are used. Although it is not necessary, sterile conditions or clean environments are highly desirable when carrying out the manufacturing processes of the invention, especially when the biological compositions are for human consumption. The manufacturing process can be adapted to meet regulatory guidelines on product safety and quality control by standard practice known in the art.

5.1.2 Electromagnetic Fields

As used herein, the terms "alternating electromagnetic field", "electromagnetic field" or "EM field" are synonymous. An electromagnetic field useful in the invention can be generated by various means well known in the art. A schematic illustration of exemplary setups are depicted respectively in FIG. 1. An electromagnetic field of a desired frequency and a desired field strength is generated by an electromagnetic wave source (3) which comprises one or more signal generators that are capable of generating electromagnetic waves, preferably sinusoidal waves, and preferably in the frequency range of 8000 MHz–13000 MHz Such signal generators are well known in the art (e.g., the HP 83721B and HP 83741A manufactured by Hewlett Packard, Palo Alto, Calif.). Signal generators capable of generating signal with a narrower frequency range can also be used. If desirable, a signal amplifier can also be used to increase the output signal, and thus the strength of the EM field.

The electromagnetic field can be applied to the culture by a variety of means including placing the yeast cells in close proximity to a signal emitter connected to a source of electromagnetic waves. Typically, the yeast cells are placed in a container which is made of material that is not an electric conductor, such as but not limited to plastic, resin, glass, and ceramic.

In one embodiment, the electromagnetic field is applied by signal emitters in the form of electrodes (4) that are submerged in a culture of yeast cells (1). In a preferred embodiment, one of the electrodes is a metal plate which is placed on the bottom of a non-conducting container (2), and the other electrode comprises a plurality of wires or tubes so configured inside the container such that the energy of the electromagnetic field can be evenly distributed in the culture. The electrodes are preferably made of copper. For an upright culture vessel, the tips of the wires or tubes are placed within 3 to 30 cm from the bottom of the vessel (i.e., approximately 2 to 10% of the height of the vessel from the bottom). Table 1 provides some typical dimensions of the electrode wires and the non-conducting container. However, the dimensions in Table 1 are provided for illustration purposes and should not be interpreted to be limiting.

TABLE 1

| height of culture medium in the non-conducting container (cm) | distance electrode wires are placed from the bottom of the container (cm) | range for distance of the electrode wires from the bottom (cm) |
|---|---|---|
| 15–20 | 3 | 3–5 |
| 20–30 | 5 | 5–7 |
| 30–50 | 7 | 7–10 |
| 50–70 | 10 | 10–15 |
| 70–100 | 15 | 15–20 |
| 100–150 | 20 | 20–30 |
| 150–200 | 30 | 25–30 |

The number of electrode wires used depends on both the volume of the culture and the diameter of the wire. For example, for a culture having a volume of 10 liter or less, two or three electrode wires having a diameter of between 0.5 to 2.0 mm can be used. For a culture volume of 10 liter to 100 liter of culture, the electrode wires or tubes can have a diameter of 3.0 to 5.0 mm. For a culture volume of 100 liter to 1000 liter, the electrode wires or tubes can have a diameter of 6.0 to 15.0 mm. For a culture having a volume greater than 1000 liter, the electrode wires or tubes can have a diameter of between 20.0 to 25.0 mm.

5.1.3 Activation of Yeast Cells

According to the invention, the method for producing activated yeast cells of the invention comprises culturing yeast cells in the presence of a series of five alternating electromagnetic (EM) fields.

The culture process can be initiated by inoculating 1000 ml of medium with an inoculum of a selected yeast strain (such as one of those described in section 5.1.1) such that the starting cell density of the culture is greater than about $1\times10^8$ cells/1000 ml. For example, *Saccharomyces cerevisiae* Hansen strain IFFI1202 can be used. The starting culture can be used to seed larger scale culture. The culture is maintained initially at 28° C. to 32° C. for 22 to 30 hours prior to exposure to the EM field(s), typically at 30° C. for 28 hours.

The culturing process may preferably be conducted under conditions in which the concentration of dissolved oxygen is between 0.025 to 0.08 mol/m$^3$, preferably 0.04 mol/m$^3$. The oxygen level can be controlled by any conventional means known in the art, including but not limited to stirring and/or bubbling.

The culture is most preferably carried out in a liquid medium which contains sources of nutrients assimilable by the yeast cells. Table 2 provides an exemplary medium for culturing the yeast cells of the invention.

TABLE 2

| Medium Composition | Quantity |
|---|---|
| Sucrose | 18 g |
| Vitamin $B_{12}$ | 20 µg |
| Vitamin $B_3$ | 40 µg |
| Vitamin H | 10 µg |
| Fetal calf serum | 35 ml |
| $KH_2PO_4$ | 0.20 g |
| $MgSO_4 \cdot 7H_2O$ | 0.25 g |
| NaCl | 0.30 g |
| $CaSO_4 \cdot 2H_2O$ | 0.20 g |
| $CaCO_3 \cdot 5H_2O$ | 4.0 g |
| Peptone | 2.5 g |
| Autoclaved water | 1000 ml |

In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.2% and 2%. These carbon sources can be used individually, or several such carbon sources may be combined in the medium. Among the inorganic salts which can be incorporated in the culture media are the customary salts capable of yielding sodium, calcium, phosphate, sulfate, carbonate, and like ions. Non-limiting examples of nutrient inorganic salts are $KH_2PO_4$, $(NH_4)_2HPO_4$, $CaCO_3$, $MgSO_4$, NaCl, and $CaSO_4$.

It should be noted that the composition of the media provided in Table 2 is not intended to be limiting. The process can be scaled up or down according to needs. Various modifications of the culture medium may be made by those skilled in the art, in view of practical and economic considerations, such as the scale of culture and local supply of media components.

In one embodiment, a series of five EM fields are applied to the culture of yeast cells, each having a different set of frequencies within a stated range, and a different set of field strengths within a stated range.

For the first EM field, which can be applied by any means known in the art, such as the apparatus described in section 5.1.2, the frequency range is 9921 to 9930 MHz. The field strength of the EM field is in the range of 220 to 240 mV/cm. The yeast culture is exposed to this first EM field for about 36 hours.

For the second EM field, the frequency range is 10121 to 10130 MHz. The field strength of the EM field is in the range of 225 to 245 mV/cm. The yeast culture is exposed to this first EM field for about 18 hours.

For the third EM field, the frequency range is 12141 to 12150 MHz. The field strength of the EM field is in the range of 235 to 255 mV/cm. The yeast culture-is exposed to this first EM field for about 38 hours.

For the fourth EM field, the frequency range is 12831 to 12840 MHz. The field strength of the EM field is in the range of 270 to 290 mV/cm. The yeast culture is exposed to this first EM field for about 24 hours.

For the fifth EM field, the frequency range is 12871 to 12880 MHz. The field strength of the EM field is in the range of 250 to 270 mV/cm. The yeast culture is exposed to this first EM field for about 20 hours.

In less preferred embodiments, the yeast cells can be cultured by exposure to these five EM fields in a different order. In other embodiments, a series of EM fields having field characteristics within the ranges stated above can be applied to activate yeast cells. The yeast cells can remain in the same container and use the same set of electromagnetic wave generator and emitters when switching from one EM field to another EM field. The activated yeast cells may be recovered from the culture by various methods known in the art, and stored at a temperature below about 0° C. to 4° C. The activated yeast cells recovered from the liquid culture may be dried and stored in powder form. Preferably, the powder form of the yeast cells comprises greater than about $1 \times 10^{10}$ yeast cells per gram.

5.1.4 Conditioning of Yeast Cells

According to the invention, performance of the activated yeast cells can be optimized by culturing the activated yeast cells in the presence of an extract from the stomach (e.g., the gastric juice) of an animal with physiology similar to the subject to which the biological composition will be administered. The inclusion of this additional conditioning process allows the activated yeast cells to adapt to and endure the acidic environment of the subject's stomach. The method for conditioning activated yeast cells of the invention comprises culturing yeast cells in such materials in the presence of a series of at least two alternating electromagnetic (EM) fields.

The culture process can be initiated by inoculating 1000 ml of a conditioning medium with about 10 g of dried activated yeasts containing about $10^{10}$ cells/gram (as prepared by the methods described in section 5.1.3). An equivalent number of yeast cells in culture can also be used as an inoculum. The conditioning medium comprises per 1000 ml about 700 ml of gastric juice of an animal and about 300 ml of wild hawthorn juice. The process can be scaled up or down according to needs.

The gastric juice of an animal can be obtained from the stomach content of a freshly slaughtered animal. Although not essential, the animal is preferably kept under a clean environment, and fed a standard diet, preferably germ-free. For example, the content of the stomach of a 120-day old pig is mixed with 2000 ml of distilled water, and allowed to settle without stirring for 6 hours. The clear liquid above is collected for use as the gastric juice used in the conditioning process. The gastric juice of a pig can be used to condition yeast cells for use in a variety of mammals, including humans. Other methods that can be used to collect the gastric juice include centrifugation or filtration of the mixture to remove debris and/or microorganisms. The gastric juice so obtained can be stored at 4° C. Preferably, the collection procedures and storage are carried out under sterile conditions.

The wild hawthorn juice is an extract of wild hawthorn fruits prepared by slicing the fruits and drying the splices in air, preferably to less than about 8% moisture (commercial dryer can be used if necessary), crushing the dried fruits to less than about 20 mesh, and mixing 1500 ml of water per 500 gram of the crushed wild hawthorn. The mixture is then allowed to settle without stirring for 6 hours, and the clear liquid above is collected for use as the wild hawthorn juice used in the conditioning process. Other methods that can be used to collect the hawthorn juice include centrifugation or filtration of the mixture. Preferably, the collection procedures and storage are carried out under sterile conditions.

The activated yeast cells are cultured in a first EM field which can be applied by the apparatus described in section 5.1.2 or any means known in the art. The frequency range of the first EM field is 12831 to 12840 MHz. The field strength is in the range of 290 to 320 mV/cm. The temperature is maintained at 28° C. to 32° C., and typically at 30° C. The yeast culture is exposed to this first EM field for about 36 to 42 hours, preferably for 36 hours.

The activated yeast cells are then cultured in a second EM field which has the following field characteristics: 12871 to 12880 MHz; field strength at about 290 to 310 mV/cm. The temperature is maintained at 28° C. to 32° C., and typically at 30° C. The yeast culture is exposed to this second EM field for about 28 to 32 hours, preferably for 30 hours.

In less preferred embodiments, the yeast cells can be cultured by exposing the culture to these EM fields in a different order. In other embodiments, a series of EM fields having field characteristics within the ranges stated above can be applied to condition the yeast cells. The yeast cells can remain in the same container and use the same set of electromagnetic wave generator and emitters when switching from one EM field to another EM field. The activated yeast cells may be recovered from the culture by various methods known in the art, and stored at a temperature below about 0° C. to 4° C.

The activated and conditioned yeast cells can be used directly in a biological composition or used as a starter culture for large scale manufacturing. The activated yeast cells recovered from the liquid culture may be dried and stored in powder form. Preferably, the powder form of the yeast cells comprises greater than about $10^{10}$ yeast cells per gram.

5.1.5 Large Scale Manufacturing

The present invention also encompasses methods of manufacturing of the biological compositions of the invention at a large scale. The activated and conditioned yeast cells as prepared by sections 5.1.3 and 5.1.4 are propagated on a large scale to make the biological compositions of the invention. The method comprises culturing the yeast cells in the presence of one or more EM fields for a period of time, diluting the growing yeast cells with fresh medium, and repeating the process. The method can be carried out as a batch process or a continuous process.

In one preferred embodiment, a set of three containers (5, 6, 7) each comprising a set of electrodes for generating an electromagnetic field as described in section 5.1.2 are set up each with 1000 liters of a culture medium. See FIG. 2. The culture medium comprises nutrients assimilable by the yeast cells as shown in Table 3.

TABLE 3

| Material | Quantity |
|---|---|
| Wild hawthorn juice | 300 liters |
| Jujube juice | 300 liters |
| Wu wei zi juice | 300 liters |
| Soybean juice | 100 liters |

The wild hawthorn juice is an extract of fresh wild hawthorn fruits prepared by washing the fruits clean, drying the fruits in air or using a commercial dryer to less than about 8% moisture, crushing the dried fruits to less than about 20 mesh, and mixing the crushed wild hawthorn with water at a ratio of 400 liters of water per 100 kg of crushed fruits. The mixture is then stirred continuously for 12 hours while the temperature is maintained at 28° C. to 30° C. The mixture is then centrifuged at 1000 rpm to collect the supernatant which is used as described above. Preferably, the procedures are carried out under sterile conditions.

The jujube juice is an extract of fresh jujube fruits prepared by washing the fruits clean, drying the fruits to less than about 8% moisture, crushing the dried fruits to less than about 20 mesh, and mixing the crushed jujube with water at a ratio of 400 liters of water per 100 kg of crushed fruits. The mixture is then stirred continuously for 12 hours while the temperature is maintained at 28° C. to 30° C. The mixture is then centrifuged at 1000 rpm to collect the supernatant which is used as described above. Preferably, the procedures are carried out under sterile conditions.

The wu wei zi juice is an extract of fresh berries of *Schisandra chinensis* plant prepared by washing the berries, drying the fruits to less than about 8% moisture, crushing the dried berries to less than about 20 mesh, and mixing the crushed berries with water at a ratio of 400 liters of water per 100 kg of crushed berries. The mixture is then stirred continuously for 12 hours while the temperature is maintained at 28° C. to 30° C. The mixture is then centrifuged at 1000 rpm to collect the supernatant which is used as described above. Preferably, the procedures are carried out under sterile conditions.

The soybean juice is prepared by washing the soybeans, drying the soybeans to less than about 8% moisture, crushing the soybeans to less than about 20 mesh, and mixing the crushed soybeans with water. For 30 kg of soybeans, 130 liters of water is used. The mixture is then stirred continuously for 12 hours while the temperature is maintained at 28° C. to 30° C. The mixture is then centrifuged at 1000 rpm to collect the supernatant which is used as described above. Preferably, the procedures are carried out under sterile conditions.

The first container is inoculated with activated and conditioned yeast cells. About 1000 g of dried yeast powder as prepared by the methods of sections 5.1.3 and 5.1.4 are added to 1000 liter of culture medium. Each gram of the dried yeast powder comprises about $10^{10}$ yeast cells. Instead of dried yeast cells, an equivalent number of yeast cells in a liquid medium can also be used.

The yeast cells in the first container (5) are then subjected to a series of two EM fields. For the first EM field, which can be applied by the apparatus described in section 5.1.2, the frequency range is at 12831 to 12840 MHz; preferably 12836 MHz. The field strength of the EM field is in the range of 300 to 320 mV/cm, preferably at 316 mV/cm. The yeast culture is exposed to this first EM field for about 16 hours. The yeast cells are then subjected to a second EM field having a frequency of 12871 to 12880 MHz, preferably 12872 MHz, and a field strength of about 310 to 330 mV/cm, preferably at 316 mV/cm. The yeast culture is exposed to this second EM field for about 12 hours. The yeast cells from the first container are then transferred to the second container which contains about 1000 liter of the culture medium. In effect, the first yeast culture is diluted by about 50% with fresh culture medium.

In the second container (6), the yeast cells are again subjected to a series of two EM fields. The frequencies used in the second container are similar to those used in the first container but the field strengths are marginally higher. The first EM field has the following field characteristics: frequency range at 12831 to 12840 MHz, preferably 12836 MHz; and field strength in the range of 330 to 350 mV/cm, preferably at 334 mV/cm. The yeast culture is exposed to this EM field for about 24 hours. The yeast cells are then subjected to a second EM field having a frequency range of 12871 to 12880 MHz, preferably 12872 MHz; and a field strength of about 320 to 340 mV/cm, preferably at 334 mV/cm. The yeast culture is exposed to this second EM field for about 12 hours. The yeast cells from the second container are then transferred to the third container which contains yet another 1000 liter of the culture medium. Again, the second yeast culture is diluted by about 50% with fresh culture medium.

In the third container (7), the yeast cells are again subjected to a series of two EM fields. The frequencies used in the third container are similar to those used in the first and second container but the field strengths are lower. The first EM field has the following field characteristics: frequency at 12831 to 12840 MHz; preferably 12836 MHz; and field strength in the range of 250 to 270 mV/cm, preferably at 263 mV/cm. The yeast culture is exposed to this EM field for about 24 hours. The yeast cells are then subjected to a second EM field having a frequency of 12871 to 12880 MHz and a field strength of about 250 to 270 mV/cm, preferably at 263 mV/cm. The yeast culture is then exposed to this second EM field for about 12 hours.

The yeast cell culture resulting from the end of this stage can be used directly as a biological composition of the invention, or used to form other compositions encompassed by the invention. Other ingredients that enhance the healthful benefits, pharmacological properties and/or organoleptic characteristics of the composition can be added. To maintain viability and freshness of the composition, it is preferred that the various downstream and packaging process be carried out below room temperature, and preferably at 0° to 4° C. The concentration of yeast cells in the medium at the end of the culture period is typically at least about $10^3$ cells per ml. Standard methods of quality control and packaging are applied to produce in one embodiment of the invention, oral compositions packaged in liquid containers each comprising about 30 to 50 ml or 100 ml of the live yeast cell culture. The concentration of yeast cells is at least $4 \times 10^3$ cells per ml or higher, for example about $10^4$ cells per ml.

In another embodiment, the activated and conditioned yeast cells can be dried as follows. The yeast cell culture is first centrifuged under 75 to 100 g for 10 to 20 minutes to remove the supernatant. The residue which may contain up to 85% moisture is dried in a first dryer at a temperature not exceeding 60±2° C. for a period of 5 minutes so that yeast cells quickly became dormant. The yeast cells were then sent to a second dryer and dried at a temperature not exceeding 65±2° C. for a period of about 8 minutes to further remove water. The dried yeast cells which may contain up to 12% moisture were then cool to room temperature. The dried yeast cells can be packaged by standard pharmaceutical methods in various solid dosage form, each containing a predetermined amount of the dried material. Preferably, the dried material comprises at least $10^6$ cells per gram.

In general, the compositions are prepared by uniformly and intimately admixing the active ingredient with liquid carriers or finely divided solid carriers.

5.1.6 Preferred Embodiments

In one preferred embodiment, the invention provides a method for preparing a biological composition comprising activated and conditioned yeast cells, said method comprising in any order the steps of:
  (a) culturing yeast cells in a first electromagnetic field or series of electromagnetic fields having a frequency at 9923 MHz and a field strength of 233 mV/cm;
  (b) culturing the yeast cells in a second electromagnetic field or series of electromagnetic fields having a frequency at 10127 MHz and a field strength of 240 mV/cm;
  (c) culturing the yeast cells in a third electromagnetic field or series of electromagnetic fields having a frequency at 12145 MHz and a field strength of 247 mV/cm;
  (d) culturing the yeast cells in a fourth electromagnetic field or series of electromagnetic fields having a frequency at 12836 MHz and a field strength of 272 mV/cm; and
  (e) culturing the yeast cells in a fifth electromagnetic field or series of electromagnetic fields having a frequency at 12872 MHz and a field strength of 252 mV/cm;

and after the last of the first five steps, the following steps in any order:
  (f) culturing the yeast cells in a liquid medium comprising wild hawthorn juice and gastric juice of a mammal in a sixth electromagnetic field or series of electromagnetic fields having a frequency at 12836 MHz and a field strength of 296 mV/cm; and
  (g) culturing the yeast cells in a liquid medium comprising wild hawthorn juice and gastric juice of a mammal in a seventh electromagnetic field or series of electromagnetic fields having a frequency at 12872 MHz and a field strength of 302 mV/cm.

The activated and conditioned yeast cells obtained at the conclusion of this method is encompassed by the invention. Preferably, the yeast cells are *Saccharomyces cerevisiae* Hansen strain IFFI1202. These yeast cells can be used in the following method of further expanding number of activated and conditioned yeast cells.

In another preferred embodiment, the invention provides a method of mass producing a biological composition comprising activated and conditioned yeast cells, said method comprising culturing the activated and conditioned yeast cells prepared by the preferred embodiment described above in this section, in a medium comprising wild hawthorn juice, jujube juice, wu wei zi juice, and soybean juice, and in the presence of one or more series of electromagnetic fields. Each series of EM fields comprises two EM fields in the order stated:
  (h) an eighth electromagnetic field having a frequency in the range of 12836 MHz and a field strength of 250–350 mV/cm; and
  (i) a ninth electromagnetic field having a frequency in the range of 12872 MHz and a field strength of 250–340 mV/cm.

The series may be repeated several times, such as three times.

5.2 Methods of Uses

5.2.1 Formulations

The biological compositions of the present invention comprise activated and conditioned live yeast cells prepared as described above, as active ingredient, and can optionally contain a pharmaceutically acceptable carrier or excipient, and/or other ingredients. Other ingredients that can be incorporated into the biological compositions of the present invention, may include, but are not limited to, herbal extracts, vitamins, amino acids, metal salts, metal chelates, coloring agents, flavor enhancers, preservatives, and the like.

In one embodiment, compositions of the present invention suitable for oral administration may be presented as discrete units such as capsules, cachets, or tablets, each containing a predetermined amount of activated and conditioned yeast cells, as a powder or granules or as a solution or a suspension in an aqueous liquid, a non-aqueous liquid, an oil-in-water emulsion, or a water-in-oil liquid emulsion. In general, the compositions are prepared by uniformly and intimately admixing the active ingredient with liquid carriers or finely divided solid carriers or both, and then, if necessary, shaping the product into the desired presentation. Such products can be used as pharmaceuticals or dietary supplements, depending on the dosage and circumstances of its use.

The oral compositions of the present invention may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets or capsules can be coated by methods well known in the art.

Liquid preparations for oral administration can take the form of, for example, solutions, syrups or suspensions, or they can be presented as a dry product for constitution with water or other suitable vehicle before use. The temperature of the liquid used to reconstitute the dried product should be less than 65° C. Such liquid preparations can be prepared by conventional means with pharmaceutically acceptable additives such as suspending agents (e.g., sorbitol syrup, cellulose derivatives or hydrogenated edible fats);emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). As described below, the preparations can also be made to resemble foods, containing buffer salts, flavoring, coloring and sweetening agents as appropriate.

Any dosage form may be employed for providing the subject with an effective dosage of the biological composition. Dosage forms include tablets, capsules, dispersions, suspensions, solutions, capsules, and the like. Generally, because of their ease of administration, tablets and capsules represent the most advantageous oral dosage unit form, in which case solid pharmaceutical carriers as described above are employed. In another embodiment, a preferred form of preparation is cell suspension, containing at least $1 \times 10^3$ yeast cells per ml. For example, a tablet may be prepared by compression or molding, optionally, with one more accessory ingredients. Compressed tablets may be prepared by compressing in a suitable machine dried activated and conditioned yeast cells in a free-flowing form such as powder or granules, optionally mixed with a binder, lubricant, inert diluent, surface active or dispersing agent. Preferably, the composition is a capsule containing 500 to 700 mg of live yeast cells (at greater than about $1 \times 10^6$ cells/g) in powder form. A preferred dose is two to four capsule per day.

In another embodiment, the biological compositions comprising activated and conditioned yeast cells can be added directly to foods so that an effective amount of yeast cells is ingested during normal meals. Any methods known to those skilled in the art may be used to add to or incorporate the biological compositions into natural or processed foods, provided that the activated and conditioned yeast cells remain viable. Preferably, the nutritional compositions of the invention are made and stored under conditions, such as temperature, from about 0° C. to 4° C. As used herein, the term "food" broadly refers to any kind of material, liquid or solid, that is used for nourishing an animal, and for sustaining normal or accelerated growth of an animal including humans. Many types of food products or beverages, such as but not limited to, fruit juice, herbal extracts, tea-based beverages, dairy products, soybean product (e.g., tofu), and rice products, can be used to form nutritional compositions comprising the activated and conditioned yeast cells of the invention.

5.2.2 Uses In Subjects with Immunodeficiency Disorders or Under Immunosuppression The present invention further provides methods of use of the biological compositions of the invention. In one embodiment, the biological composition is used as a medicament for treatment, modification, and alleviation of immunodeficiency disorders or immunosuppression. In another embodiment, the biological composition is used as a dietary supplement, health food, or health drink. The methods comprise administering an effective amount of the biological composition to a subject in need. The biological composition may be administered orally, in liquid or solid form, or enterally through a feeding tube. As used herein, the term "an effective amount" means an amount sufficient to provide a therapeutic or healthful benefit in the context of immunodeficiency disorders or immunosuppression.

According to the invention, the biological composition can produce a healthful benefit in a subjects inflicted with immunodeficiency disorders or immunosupression. Preferably, the subject is a human being. The subject in need is one who is diagnosed to be under a state of immunosuppression or with symptoms at any stage of the disorder. As used herein, the terms "immunodeficiency disorders" and "immunosuppression" include but is not limited to congenital immunodeficiency disorders, and acquired immunodeficiency disorders or immunosuppressed conditions including those caused by hereditary and metabolic diseases (e.g., diabetes, Down syndrome, kidney failure, malnutrition, sickle cell anemia), chemicals and treatments that suppress the immune system (e.g., cancer chemotherapy, coricosteroids, immunosuppressive drugs, radiation therapy), infections (e.g., chickenpox, cytomegalovirus infection, German measles, HIV infection (AIDS), infectious mononucleosis, measles, severe bacterial or fungal infection, severe tuberculosis), blood diseases and cancer (e.g., agranulocytosis, aplastic anemia, histiocytosis, leukemia, lymphoma, myelofibrosis, myeloma), bums, removal of the spleen, alcoholic cirrhosis, chronic hepatitis, normal aging, sarcoidosis, and systemic lupus erythematosus.

The subject may be a patient who is receiving concurrently other treatment modalities against the immunodeficiency disorder or corresponding symptoms. The subject may be a patient who had undergone a regimen of treatment (e.g., blood transfusions and bone marrow transplants) and who appears to be clinically immunocompetent. The biological composition of the invention can be administered adjunctively with any of the treatment modalities, such as but not limited to antibiotics, drug therapy, vaccines, blood transfusions, and bone marrow transplants.

The subject may be one who has not yet been diagnosed with the immunodeficiency disorder but are predisposed to or at high risk of developing the immunodeficiency disorder as a result of genetic factors and/or environmental factors. The subject may also be one who displays characteristics that are associated with a high risk of immunodeficiency disorder, such as those with a weakened immune system, undergoing anti-inflammatory drugs, malnourished, or under stress.

Depending on the subject, the therapeutic and healthful benefits range from modifying, inhibiting, retarding, or palliating the symptoms of immunosuppression or the immunodeficiency disorder, increasing the numbers of different classes of circulating white blood cells, improving the quality of life of the subject, and/or reducing the probability of relapse after a successful course of treatment (e.g., blood transfusions, bone marrow transplants). The signs and symptoms associated with immunodeficiency disorders or immunosuppression include, but are not limited to, pale, thin appearance, skin rash, pustules, eczema, broken blood vessels, hair loss, purple blotches, redness of the lining of the eye (conjunctivitis), enlarged lymph nodes, scarred and perforated eardrums, crusted nostrils, diarrhea, extreme gassiness, and weight loss.

In particular, the invention provides a method for promoting activation and proliferation of white blood cells or increasing the white blood cell count in a subject, such as a human, comprising administering orally to the subject a biological composition of the invention. The invention also provide a method for shortening the time of recovery of a subject under immunosuppression or suffering from immunodeficiency disorders, comprising administering orally to the subject a biological composition of the invention.

The effective dose for the subject will also vary with the condition to be treated and the severity of the condition to be treated. The dose, and perhaps the dose frequency, will also vary according to the age, body weight, and response of the individual patient. In general, the total daily dose range of activated and conditioned yeast cells is from about $10^5$ to $5 \times 10^6$, preferably $4 \times 10^5$ to about $13 \times 10^5$ cells administered in single or divided doses orally. For example, a preferred oral daily dose range should be from about $7 \times 10^5$ to about $9 \times 10^5$ cells, while for use as a dietary supplement, the oral daily dose should be about $5 \times 10^5$ to about $6 \times 10^5$ cells. A course of treatment should be at least 13 weeks. It may be necessary to use dosages outside these ranges in some cases as will be apparent to those skilled in the art. The yeast cells can be used for a period of time until the symptoms and/or infection by the bacteria and viruses are under control, or when the disease has regressed partially or completely. Further, it is noted that the nutritionist, dietician, clinician or treating physician will know how and when to interrupt, adjust, or terminate use of the biological composition as a medicament or dietary supplement in conjunction with individual patient response.

The effect of the biological compositions of the invention on development and severity of immunodeficiency disorders or immunosuppression can be monitored by any methods known to one skilled in the art, including but not limited to measuring: a) changes in the number, biological activity, and morphology of the different types of white blood cells using tests well known in the art; and b) changes in levels of biological markers such as cytokines.

The invention is further defined by reference to the following example describing in detail the animal trials conducted to study the efficacy and safety of activated and conditioned yeast cells of the invention.

6. EXAMPLE

The following example illustrates the benefit of a biological composition of the invention in a Wistar rat model of an immunodeficiency disorder or immunsuppression.

Cyclophosphamide, a commonly used cancer chemotherapeutic agent, reduces the number of white blood cells in patients undergoing treatment. The number of white blood cells in Wistar rats fed with cyclophosphamide are reduced in a similar manner as in human cancer patients treated with cyclophosphamide. Accordingly, this experiment has incorporated the use of cyclophosphamide in setting up a Wistar rat model having a reduced number of white blood cells.

The biological composition comprising $10^3$ cells per ml of activated and conditioned yeast cells of the strain *Saccharomyces cerevisiae* Hansen strain IFFI1202 were prepared by the methods described in section 5.1 and subsections therein.

6.1 Animal Preparation

The animals used for the experiments are Wistar rats (obtainable from the Laboratory Animal Unit, The Chinese Military Academy of Medical Sciences), 3 to 4 months old, with an average body weight of about 80 g to 100 g. An equal number of males and females were used. The rats were divided into three experimental groups and one control group of ten rats per group. The four groups were triplicated (i.e., using a total of 120 rats).

6.2 Experimental Design

On the $1^{st}$ day, the rats in the three experimental groups (AY, NY, and CK1) were fed 60 mg per kg body weight of cyclophosphamide. On the $10^{th}$ day, the rats in the three experimental groups were fed 20 mg per kg body weight of cyclophosphamide. On the $14^{th}$ day, the rats in the three experimental groups were again fed 20 mg per kg body weight of cyclophosphamide. On the $21^{st}$ day, the rats in the three experimental groups were fed 30 mg per kg body weight of cyclophosphamide. The rats for kept for another 7 days, or a total of 28 days.

During the same time, from the first day to the twenty-eighth day of the experiments, the rats in group AY were fed 1 ml of the biological composition two times per day, 12 hours apart, the rats in group NY were fed 1 ml of untreated yeast cells two times per day, and the rats in group CK1 were fed 1 ml of physiological saline two times per day.

The rats in group CK2 were not fed with any chemotherapeutic agent and only 1 ml of physiological saline twice a day for 28 days.

Blood from the rats were obtained by artery tail bleed. Using a haemocytometer, the number of white blood cells in the blood of the rats were determined on day 1, before treatment, and 7 days, 14 days, 21 days, and 28 days after treatment.

6.3 Results

Table 4 shows the different number of white blood cells in the rats of the various treatment and control groups.

TABLE 4

| | | Number of white blood cells ($\times 10^3/mm^3$) | | | | |
|---|---|---|---|---|---|---|
| | no. of animals | before treatment | 7 days after treatment | 14 days after treatment | 21 days after treatment | 28 days after treatment |
| AY | 10 × 3 | 14.2 ± 3.2 | 8.4 ± 2.6 | 9.3 ± 2.8 | 12.8 ± 2.7 | 14.3 ± 2.4 |
| NY | 10 × 3 | 14.2 ± 3.2 | 2.6 ± 0.33 | 2.4 ± 0.27 | 2.1 ± 0.22 | 3.6 ± 0.37 |
| CK1 | 10 × 3 | 14.2 ± 3.3 | 2.6 ± 0.37 | 2.3 ± 0.29 | 2.1 ± 0.23 | 3.7 ± 0.38 |
| CK2 | 10 × 3 | 14.2 ± 3.2 | 14.2 ± 3.4 | 14.2 ± 3.3 | 14.7 ± 3.2 | 14.4 ± 3.2 |

The rats which received 1 ml of the biological composition of the invention two times per day (group AY) showed the smallest reduction in number of white blood cells (i.e., four times more) as compared to those rats which received 1 ml of untreated yeast cells two times per day (group NY) and those rats which received 1 ml of physiological saline two times per day (group CK1). Further, the number of white blood cells in the rats of group AY began to recover after 2 weeks of treatment with the biological composition despite being continuously fed with cyclophosphamide. By the end of 4 weeks of treatment, the number of white blood cells in the rats of group AY returned to the same number as it was before being fed cyclophosphamide. In contrast, the number of white blood cells in the rats of group NY and CK1 remained low until the end of the experiment.

7. EXAMPLE

The following example illustrates the benefit of a biological composition of the invention in a Beagle canine model of an immunodeficiency disorder or immunosuppression.

Cyclophosphamide, a commonly used cancer chemotherapeutic agent, reduces the number of white blood cells in patients undergoing treatment. The number of white blood cells in Beagles intravenously injected with cyclophosphamide are reduced in a similar manner as that in human cancer patients treated with cyclophosphamide. Accordingly, this experiment has incorporated the use of cyclophosphamide in setting up a Beagle canine model having a reduced number of white blood cells.

The biological composition comprising $10^3$ cells per ml of activated and conditioned yeast cells of the strain *Saccharomyces cerevisiae* Hansen strain IFFI 1202 were prepared by the methods described in section 5.1 and subsections therein.

7.1 Animal Preparation

The animals used for the experiments are Beagles (obtainable from the Laboratory Animal Unit, The Chinese Military Academy of Medical Sciences), 12 to 14 months old. An equal number of males and females were used. The dogs were divided into three experimental groups and one control group of ten dogs per group (i.e., using a total of 40 dogs).

7.2 Experimental Design

On the $1^{st}$ day, the dogs in the three experimental groups (AY, NY, and CK1) were intravenously injected with 10 mg per kg body weight of cyclophosphamide. On the $3^{rd}$ day, the dogs in the three experimental groups were intravenously injected with 10 mg per kg body weight of cyclophosphamide. On the $14^{th}$ day, the dogs in the three experimental groups were intravenously injected with 15 mg per kg body weight of cyclophosphamide. The dogs were kept for another 14 days, or a total of 28 days.

During the same time, from the first day to the twenty-eighth day of the experiments, the dogs in group AY were fed 10 ml of the biological composition two times per day, 12 hours apart, the dogs in group NY were fed 10 ml of untreated yeast cells two times per day, and the dogs in group CK1 were fed 10 ml of physiological saline two times per day.

The dogs in group CK2 were not fed with any cyclophosphamide but only 10 ml of physiological saline twice a day for 28 days.

Venous blood from the dogs were obtained. Using a haemocytometer, the number of white blood cells in the blood of the dogs were determined on day 1, before treatment, and 7 days, 14 days, 21 days, and 28 days after treatment.

7.3 Results

Table 5 shows the different number of white blood cells in the dogs of the various treatment and control groups.

TABLE 5

| | Number of white blood cells ($\times 10^3/mm^3$) | | | | | |
|---|---|---|---|---|---|---|
| | no. of animals | before treatment | 7 days after treatment | 14 days after treatment | 21 days after treatment | 28 days after treatment |
| AY | 10 | 16.9 ± 3.4 | 10.7 ± 2.7 | 12.5 ± 2.3 | 14.8 ± 2.4 | 17.3 ± 2.5 |
| NY | 10 | 17.4 ± 3.2 | 4.4 ± 1.3 | 5.5 ± 1.7 | 7.2 ± 1.7 | 8.8 ± 1.7 |
| CK1 | 10 | 17.7 ± 3.3 | 4.6 ± 1.4 | 5.8 ± 1.6 | 7.7 ± 1.4 | 8.7 ± 1.5 |
| CK2 | 10 | 17.4 ± 3.2 | 17.6 ± 3.4 | 17.3 ± 3.0 | 17.5 ± 3.1 | 17.7 ± 3.3 |

The dogs which received 10 ml of the biological composition of the invention two times per day (group AY) showed the smallest reduction in number of white blood cells (i.e., four times more) as compared to those dogs which received 10 ml of untreated yeast cells two times per day (group NY) and those dogs which received 10 ml of physiological saline two times per day (group CK1). Further, the number of white blood cells in the dogs of group AY began to recover after 2 weeks of treatment with the biological composition despite being continuously fed with cyclophosphamide. By the end of 4 weeks of treatment, the number of white blood cells in the dogs of group AY returned to the same, in fact, even greater in number as it was before being fed cyclophosphamide. In contrast, the number of white blood cells in the dogs of group NY and CK1 remained low until the end of the experiment.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A biological composition comprising activated yeast cells, wherein said activated yeast cells are cells of *Saccharomyces cerevisiae* Hansen strain IFFI1202 and are characterized by their ability to increase the number of white blood cells in an immunodeficient or immunosuppressed subject as compared to yeast cells of said strain not having been so activated, wherein said activated yeast cells are prepared by using yeast cells of *Saccharomyces cerevisiae* Hansen strain IFFI1202 in a method comprising in any order the steps of:
    (a) culturing said yeast cells in a first electromagnetic field or series of electromagnetic fields having a frequency in the range of 9,921 to 9,930 MHz and a field strength in the range of 220 to 240 mV/cm;
    (b) culturing said yeast cells in a second electromagnetic field or series of electromagnetic fields having a frequency in the range of 10,121 to 10,130 MHz and a field strength in the range of 225 to 245 mV/cm;
    (c) culturing said yeast cells in a third electromagnetic field or series of electromagnetic fields having a frequency in the range of 12,141 to 12,150 MHz and a field strength in the range of 235 to 255 mV/cm;
    (d) culturing said yeast cells in a fourth electromagnetic field or series of electromagnetic fields having a frequency in the range of 12,831 to 12,840 MHz and a field strength in the range of 270 to 290 mV/cm; and
    (e) culturing said yeast cells in a fifth electromagnetic field or series of electromagnetic fields having a frequency in the range of 12,871 to 12,880 MHz and a field strength in the range of 250 to 270 mV/cm.

2. The biological composition of claim 1, wherein the activated yeast cells are at a concentration of about $10^3$ cells per ml.

3. The biological composition of claim 1, wherein the activated yeast cells are dried.

4. A method for preparing a biological composition comprising activated yeast cells, wherein said activated yeast cells are cells of *Saccharomyces cerevisiae* Hansen strain IFFI1202 and are characterized by their ability to increase the number of white blood cells in an immunodeficient or immunosuppressed subject as compared to yeast cells of said strain not having been so activated, said method comprising providing yeast cells of *Saccharomyces cerevisiae* Hansen strain IFFI1202, and in any order the steps of:

(a) culturing said yeast cells in a first electromagnetic field or series of electromagnetic fields having a frequency in the range of 9,921 to 9,930 MHz and a field strength in the range of 220 to 240 mV/cm;

(b) culturing said yeast cells in a second electromagnetic field or series of electromagnetic fields having a frequency in the range of 10,121 to 10,130 MHz and a field strength in the range of 225 to 245 mV/cm;

(C) culturing said yeast cells in a third electromagnetic field or series of electromagnetic fields having a frequency in the range of 12,141 to 12,150 MHz and a field strength in the range of 235 to 255 mV/cm;

(d) culturing said yeast cells in a fourth electromagnetic field or series of electromagnetic fields having a frequency in the range of 12,831 to 12,840 MHz and a field strength in the range of 270 to 290 mV/cm; and (e) culturing said yeast cells in a fifth electromagnetic field or series of electromagnetic fields having a frequency in the range of 12,871 to 12,880 MHz and a field strength in the range of 250 to 270 mV/cm.

* * * * *

UNITED STATES PATENT AND TRADEMARK OFFICE
CERTIFICATE OF CORRECTION

PATENT NO. : 7,256,026 B2 Page 1 of 1
APPLICATION NO. : 10/185276
DATED : August 14, 2007
INVENTOR(S) : Ling Yuk Cheung It is certified that error appears in the above-identified patent and that said Letters Patent is hereby corrected as shown below:

In column 6, line 39, the term "S2.503" should read --AS2.503--;

In column 9, line 20, the expression "culture-is" should read --culture is--;

In column 15, line 60, the term "immunosupression" should read --immunosuppression--; and In column 16, line 11, the term "bums' should read --burns--.

Signed and Sealed this

Sixth Day of November, 2007

JON W. DUDAS
*Director of the United States Patent and Trademark Office*